United States Patent
Schaub et al.

(10) Patent No.: US 9,085,526 B2
(45) Date of Patent: Jul. 21, 2015

(54) PROCESS FOR PREPARING CARBOXYLIC ACID ESTERS

(71) Applicant: BASF SE, Ludwigshafen (DE)

(72) Inventors: Thomas Schaub, Neustadt (DE); Stefan Rüdenauer, Worms (DE); Daniel Schneider, Frankenthal (DE); Rocco Paciello, Bad Dürkheim (DE)

(73) Assignee: BASF SE, Ludwigshafen (DE)

( * ) Notice: Subject to any disclaimer, the term of this patent is extended or adjusted under 35 U.S.C. 154(b) by 63 days.

(21) Appl. No.: 13/943,844

(22) Filed: Jul. 17, 2013

(65) Prior Publication Data

US 2014/0024854 A1    Jan. 23, 2014

Related U.S. Application Data

(60) Provisional application No. 61/672,306, filed on Jul. 17, 2012.

(51) Int. Cl.
*C07C 67/00*    (2006.01)
*C07C 67/40*    (2006.01)

(52) U.S. Cl.
CPC ........... *C07C 67/40* (2013.01); *C07C 67/00* (2013.01)

(58) Field of Classification Search
CPC ................. C07C 67/00; C07C 69/24
See application file for complete search history.

(56) References Cited

U.S. PATENT DOCUMENTS

2011/0319636 A1*  12/2011  Nordstrom et al. ........... 548/537

FOREIGN PATENT DOCUMENTS

| WO | WO-2010058004 A1 | 5/2010 |
| WO | WO-2012052996 A2 | 4/2012 |
| WO | PCT/EP2013/057654 | 10/2013 |

OTHER PUBLICATIONS

Nielsen, Martin, et al., "Towards a Green Process for Bulk-Scale Synthesis of Ethyl Acetate: Efficient Acceptorless Dehydrogenation of Ethanol", Angew. Chem., vol. 124, (2012), pp. 5809-5811.
U.S. Appl. No. 13/864,774, filed Apr. 20, 2012, Paciello et al.
Murahashi, Shun-Ichi, et al., "Ruthenium Catalyzed Transformation of Alcohols to Esters and Lactones", Tetrahedron Letters, vol. 22, No. 52, (1981), pp. 5327-5330.
Murahashi, Shun-Ichi, et al., "Ruthenium-Catalyzed Oxidative Transformation of Alcohols and Aldehydes to Esters and Lactones", J. Org. Chem., vol. 52, (1987), pp. 4319-4327.
Blum, Yigal, et al., "Catalytically Reactive ($\eta^4$-Tetracyclone)(CO)$_2$(h)$_2$Ru and Related Complexes in Dehydrogenation of Alcohols to Esters", Journal of Organometallic Chemistry, vol. 282, (1985), pp. C7-C10.
Dobereiner, Graham E., et al., "Dehydrogenation as a Substrate-Activating Strategy in Homogenous Transition-Metal Catalysis", Chem. Rev., vol. 110, (2010), pp. 681-703.
Zhang, Jing, et al., "Facile Conversion of Alcohols into Esters and Dihydrogen Catalyzed by New Ruthenium Complexes", J. Am. Chem. Soc., vol. 127, (2005), pp. 10840-10841.
Sølvhøj, Amanda, et al., "Dehydrogenative Coupling of Primary Alcohols to Form Esters Catalyzed by a Ruthenijm N-Heterocyclic Carbene Complex", Organometallics, vol. 30, (2011), pp. 6044-6048.
Del Pozo, Carolina, et al., "Pincer-Type Pyridine-Based N-Heterocyclic Carbene Amine Ru(II) Complexes as Efficient Catalysts for Hydrogen Transfer Reactions", Organometallics, vol. 30, (2011), pp. 2180-2188.
Zhang, Jing, et al., "Electron-Rich PNP- and PNN-Type Ruthenium(II) Hydrido Borohydride Pincer Complexes. Synthesis, Structure, and Catalytic Dehydrogenation of Alcohols and Hydrogenation of Esters", Organometallics, vol. 30, (2011), pp. 5716-5724.
Nielsen, Martin, et al., "Towards a Green Process for Bulk-Scale Synthesis of Ethyl Acetate: Efficient Acceptorless Dehydrogenation of Ethanol", Angew. Chem., vol. 124, (2012), pp. 1-4.
International Preliminary Report on Patentablity for PCT/EP2013/064957 issued Jan. 20, 2015.

* cited by examiner

*Primary Examiner* — Rosalynd Keys
*Assistant Examiner* — Jennifer C Sawyer
(74) *Attorney, Agent, or Firm* — Drinker Biddle & Reath LLP

(57) ABSTRACT

The present invention relates to a process for preparing carboxylic acid esters, comprising the reaction of at least one primary monoalcohol or of a mixture of a primary monoalcohol and at least one alcohol different therefrom in the presence of a transition metal carbene complex catalyst K which has, as central atom M, at least one transition metal atom of group 8, 9 or 10 of the Periodic Table of the Elements (IUPAC) and at least one monodentate N-heterocyclic carbene ligand, in the presence of a base, wherein the catalyst K is prepared by reacting a transition metal compound V which has at least one transition metal atom of group 8, 9 or 10 of the Periodic Table of the Elements (IUPAC), but no carbene ligand, with an imidazolium salt in the presence of the primary monoalcohol and the base, the reaction being carried out without dilution.

22 Claims, No Drawings

PROCESS FOR PREPARING CARBOXYLIC ACID ESTERS

RELATED APPLICATIONS

This application claims benefit (under 35 USC 119(e)) of U.S. Provisional Application Ser. No. 61/672,306, filed Jul. 17, 2012, which is incorporated herein by reference in its entirety.

BACKGROUND OF THE INVENTION

The present invention relates to a process for preparing carboxylic acid esters by reacting at least one primary monoalcohol or a mixture of a primary monoalcohol and at least one alcohol different therefrom in the presence of a transition metal carbene complex catalyst K.

Carboxylic acid esters are important chemical compounds which are used for example as solvents, plasticizers, and fragrances and aroma substances. There are various methods for preparing them, the reaction of a carboxylic acid with an alcohol being the most conventional:

Since this is an equilibrium reaction which in most cases is acid-catalyzed, the water or the carboxylic acid ester has to be removed from the reaction mixture in order to achieve high yields. Particularly in the case of low-boiling carboxylic acids and low-boiling alcohols, undesired azeotropes are often formed in the process, which hinder separation.

Another way of preparing carboxylic acid esters is the reaction of an acid anhydride with an alcohol:

In this process one equivalent of the carboxylic acid is formed, which likewise has to be separated off. Here too, azeotropes often form, and moreover two equivalents of the carboxylic acid are required for one equivalent of the carboxylic acid ester.

Another way of preparing carboxylic acid esters is the transition metal complex-catalyzed reaction of alcohols with dehydrogenation, referred to below as direct ester formation. Here, the starting materials used are only alcohols, where at least one of the two reactants must have a primary OH group, i.e. a $CH_2OH$ group:

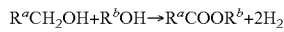

In this type of carboxylic acid ester synthesis, no carboxylic acid need be used, which is advantageous since the lower carboxylic acids in particular have an unpleasant odor. Moreover, no water is formed during the reaction, which simplifies the distillative work-up of the reaction mixture. By virtue of the fact that the reaction conditions can be kept very mild, moreover, only a few by-products are formed.

The conversion of primary alcohols to carboxylic acid esters with catalysis using transition metal complexes is described many times in the literature.

Tetrahedron Lett. 1981, 22, 5327-5330 and J. Org. Chem. 1987, 52, 4319-4327 describe the use of ruthenium complexes with phosphane ligands as catalysts for preparing carboxylic acid esters and lactones from primary alcohols.

J. Organomet. Chem. 1985, 282, C7-C10 describes catalysts for preparing carboxylic acid esters from primary alcohols using a ruthenium complex with tetraphenylcyclopentadienone ligand.

Chem. Rev. 2010, 110, 681-703 describes various transition metal complex catalysts for direct ester formation from primary alcohols.

Organometallics 2011, 30, 2180-2188, Organometallics 2011, 30, 5716-5724 and J. Am. Chem. Soc. 2005, 127, 10840-10841 describe ruthenium pincer complexes for the catalysis of the direct esterification of primary alcohols.

M. Nielsen et al., Angew. Chem. 2012, 124 describes ruthenium and iridium complex catalysts with polydentate organonitrogen and organophosphorus ligands for the synthesis of ethyl acetate from ethanol.

Organometallics 2011, 30, 6044-6048 describes ruthenium complex compounds based on N-heterocyclic carbenes as catalysts in the direct ester formation from primary alcohols. A phosphate is advantageously added to the ruthenium complex.

A disadvantage of the described methods for synthesizing carboxylic acid esters is that the transition metal complex catalysts used have to be prepared by complex syntheses and optionally have to be isolated. Moreover, oxidation-sensitive and expensive phosphane ligands are often used, which necessitates a complex reaction implementation under inert conditions. Furthermore, the procedure is predominantly carried out in relatively large amounts of an added solvent, as a result of which the reaction mixture has to be worked-up in a complex manner and the space-time yield is reduced.

The object of the present invention is to provide a process for the transition-metal-complex-catalyzed direct ester formation from primary monoalcohols or from mixtures of a primary monoalcohol and at least one alcohol different therefrom.

BRIEF SUMMARY OF THE INVENTION

Surprisingly, it has now been found that this object is achieved by a process in which a primary monoalcohol or a mixture of a primary monoalcohol and at least one alcohol different therefrom is reacted in the presence of a base and at least one transition metal carbene complex catalyst K defined in more detail below of a transition metal atom of group 8, 9 or 10 of the Periodic Table of the Elements (IUPAC) without dilution, where the catalyst K is prepared by reacting a suitable, non-carbenoid transition metal compound V with an imidazolium salt in the presence of the primary monoalcohol and the base.

DETAILED DESCRIPTION OF THE INVENTION

Accordingly, the present invention relates to a process for preparing carboxylic acid esters, comprising the reaction of at least one primary monoalcohol or of a mixture of a primary monoalcohol and at least one alcohol different therefrom in the presence of a transition metal carbene complex catalyst K which has, as central atom M, at least one transition metal atom of group 8, 9 or 10 of the Periodic Table of the Elements (IUPAC) and at least one monodentate N-heterocyclic carbene ligand, in the presence of a base, wherein the catalyst K is prepared by reacting a transition metal compound V which has at least one transition metal atom of group 8, 9 or 10 of the Periodic Table of the Elements (IUPAC), but no carbene ligand, with an imidazolium salt in the presence of the primary monoalcohol and the base, the reaction being carried out without dilution.

Advantages of the process according to the invention are primarily the mild reaction conditions, the low formation of by-products with simultaneously high space-time yield. Moreover, in this way it is possible to avoid the catalyst system having to be prepared separately. A further advantage is the simplified work-up of the reaction mixture since, on account of the reaction implementation without dilution, no solvent has to be separated off. Moreover, the low oxidation sensitivity of the catalyst system permits a reaction implementation even under non-inert conditions. Moreover, the process avoids the use of lower carboxylic acids, which have an unpleasant odor.

In the process according to the invention, at least one catalyst K which comprises at least one transition metal atom of group 8, 9 or 10 of the Periodic Table of the Elements (IUPAC) is used. The transition metals of group 8, 9 and 10 of the Periodic Table of the Elements (IUPAC) include in particular iron, cobalt, nickel, ruthenium, rhodium, palladium, osmium, iridium and platinum. Preference is given to catalysts K which comprise at least one transition metal atom which is selected from ruthenium and iridium. A particularly preferred transition metal is ruthenium.

The catalyst K has at least one, e.g. 1, 2, 3 or 4, N-heterocyclic carbene ligands. Suitable N-heterocyclic carbene ligands are primarily imidazole ligands in which the carbon in the 2 position is the carbenoid donor atom. These include in particular those of the formula (I),

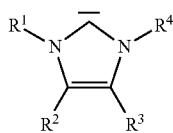

in which
$R^1$ and $R^4$ independently of one another are $C_1$-$C_{10}$-alkyl, $C_3$-$C_{10}$-cycloalkyl, 5- to 10-membered heteroaryl which has 1, 2 or 3 heteroatoms selected from O, N and S as ring members, or aryl, where the four last-mentioned substituents are unsubstituted or can be substituted with one or more substituents selected from halogen, $C_1$-$C_{10}$-alkoxy, CN, $C_1$-$C_{10}$-alkyl, $C_3$-$C_{10}$-cycloalkyl, phenyl and naphthyl;
$R^2$ and $R^3$ independently of one another are hydrogen or have one of the meanings given for $R^1$ or $R^4$.

Here and below, the prefix "$C_p$-$C_q$" used for the definition of substituents indicates the number of possible carbon atoms of the substituent.

Within the context of the present invention, unless stated otherwise, the following general definitions are applicable for the terms used in connection with the substituents:

"$C_1$-$C_{10}$-Alkyl" is a linear or branched alkyl radical having 1 to 10 carbon atoms. Examples of $C_1$-$C_{10}$-alkyl are methyl, ethyl, n-propyl, isopropyl, n-butyl, 2-butyl, isobutyl, tert-butyl (2-methylpropan-2-yl), n-pentyl (amyl), 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl, decyl and constitutional isomers thereof.

"$C_3$-$C_{10}$-Cycloalkyl" is a mono-, di-, tri- or tetracyclic alkyl radical having 3 to 10 carbon atoms. Examples are cyclopropyl, cyclobutyl, cyclopentyl, cyclohexyl, cycloheptyl, cyclooctyl and adamantyl.

"Aryl" is an aromatic hydrocarbon radical which may be substituted or unsubstituted. Examples of unsubstituted aryl are phenyl, 1-naphthyl, 2-naphthyl and 9-anthryl. Examples of aryl which can be substituted with one or more $C_1$-$C_{10}$-alkyl radicals, as defined above, are 2,6-di(isopropyl)phenyl, o-tolyl, m-tolyl, p-tolyl and mesityl.

"$C_1$-$C_{10}$-Alkoxy" is an alkyl group having 1 to 10 carbon atoms bonded by an oxygen atom. Examples are methoxy, ethoxy, n-propoxy, 1-methylethoxy (isopropoxy), n-butoxy, 1-methylpropoxy (sec-butoxy), 2-methylpropoxy (isobutoxy), 1,1-dimethylethoxy (tert-butoxy), n-pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, 2-ethylpropoxy, n-hexoxy, 1-methylpentoxy, 2-methylpentoxy, 3-methylpentoxy, 4-methylpentoxy, 1-ethylbutoxy, 2-ethylbutoxy, 3-ethylbutoxy, 1,2-dimethylbutoxy, 1,3-dimethylbutoxy, 2,3-dimethylbutoxy, 1-ethyl-2-methylpropoxy and 1-isopropylpropoxy.

"5- to 10-membered heteroaryl" is a mono- or bicyclic 5- to 10-membered aromatic ring which has 1, 2 or 3 heteroatoms selected from O, N and S as ring members. Examples are thienyl, benzothienyl, 1-naphthothienyl, thianthrenyl, furyl, benzofuryl, pyrrolyl, imidazolyl, pyrazolyl, pyridyl, pyrazinyl, pyrimidinyl, pyridazinyl, indolyl, isoindolyl, indazolyl, purinyl, isoquinolinyl, quinolinyl, acridinyl, naphthyridinyl, quinoxalinyl, quinazolinyl, cinnolinyl, piperidinyl, carbolinyl, thiazolyl, oxazolyl, isothiazolyl and isoxazolyl.

"Aliphatic olefins" are linear or branched, mono- or polyunsaturated hydrocarbons having in general 2 to 10 carbon atoms. Examples are ethene, propene, 1-butene, 2-butene, 1,3-butadiene and 2-methylprop-1-ene.

"Cycloolefins" are cyclic, mono- or polyunsaturated hydrocarbons having in general 4 to 10 carbon atoms. Examples are cyclobutene, cyclopentene, cyclohexene and 1,5-cyclooctadiene.

"Carbocyclic aromatics" are aromatic compounds having in general 6 to 10 carbon atoms which are unsubstituted or mono- or polysubstituted with alkyl radicals. Examples are benzene, naphthalene and p-cymene.

"Heteroaromatics" are unsubstituted or substituted aromatic compounds having in general 5 to 10 ring atoms which have at least one heteroatom which is selected from O, N and S. Examples are furan, pyrrole, thiophene, imidazole, pyrazole, oxazole, isoxazole and thiazole.

"Aldehydes" are linear or branched aldehydes which have in general 1 to 10 carbon atoms. Examples are formaldehyde, acetaldehyde and propionaldehyde.

"Ketones" are linear or branched ketones which have in general 3 to 10 carbon atoms. Examples are acetone, butanone, 2-pentanone and 3-pentanone.

"$C_1$-$C_{10}$-Carboxylates" are anions of saturated or unsaturated carboxylic acids having 1 to 10, in particular 1 to 4, carbon atoms. Examples of $C_1$-$C_{10}$-carboxylate are formate, acetate, acrylate, methacrylate and propionate.

"$C_1$-$C_{10}$-Alkoxides" are radicals of linear or branched alcohols having 1 to 10, in particular 1 to 4, carbon atoms. Examples are methoxide, ethoxide, propoxide, n-butylate, 2-butylate and tert-butylate.

In formula (I), the variables $R^1$, $R^2$, $R^3$ and $R^4$, independently of one another and in particular in combination, have the following meanings:

In formula (I), $R^1$ and $R^4$, independently of one another, are preferably a radical selected from $C_1$-$C_{10}$-alkyl, $C_3$-$C_{10}$-cycloalkyl, benzyl and phenyl, where the phenyl ring is unsubstituted in the two last-mentioned radicals or is mono- or polysubstituted, e.g. mono-, di- or trisubstituted, with $C_1$-$C_3$-alkyl. In particular, $R^1$ and $R^4$ are $C_1$-$C_{10}$-alkyl, specifically $C_1$-$C_6$-alkyl.

In formula (I), $R^2$ and $R^3$, independently of one another, are preferably a radical selected from hydrogen, $C_1$-$C_{10}$-alkyl, $C_3$-$C_{10}$-cycloalkyl, benzyl and phenyl, where the phenyl ring in the two last-mentioned groups is unsubstituted or is mono- or polysubstituted, e.g. mono-, di- or trisubstituted, with $C_1$-$C_3$-alkyl. In particular, $R^2$ and $R^3$ are hydrogen or $C_1$-$C_{10}$-alkyl, specifically hydrogen or $C_1$-$C_6$-alkyl and very specifically hydrogen.

Besides at least one monodentate n-heterocyclic carbene ligand, the catalyst K can have at least one further ligand L. Ligands L are preferably selected from CO, hydride, aliphatic olefins, cycloolefins, carbocyclic aromatics, in particular benzene, naphthalene and p-cymene, heteroaromatics, in particular furan, pyrrole, imidazole and pyrazole, aldehydes, in particular formaldehyde, acetaldehyde and propionaldehyde, ketones, in particular acetone, butanone, 2-pentanone and 3-pentanone, halides, $C_1$-$C_{10}$-carboxylate, methylsulfonate, methyl sulfate, trifluoromethyl sulfate, tosylate, mesylate, cyanide, isocyanate, cyanate, thiocyanate, hydroxide, $C_1$-$C_{10}$-alkoxide, cyclopentadienide, pentamethylcyclopentadienide and pentabenzylcyclopentadienide.

Particularly preferred ligands L are p-cymene, chloride, CO, hydride, $C_1$-$C_{10}$-alkoxide and $C_1$-$C_{10}$-carboxylate.

Imidazolium salts which can be used in the process according to the invention are primarily imidazolium salts of the general formula (II)

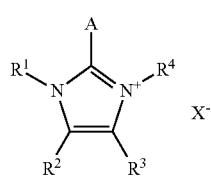

(II)

in which $R^1$, $R^2$, $R^3$ and $R^4$ have the meanings specified above, in particular the meanings indicated therein as being preferred, particularly or especially, A is H or COO$^-$ and X$^-$ is the equivalent of an anion, in particular halide, $C_1$-$C_{10}$-carboxylate, benzoate, MeC$_6$H$_4$COO$^-$, tosylate, methanesulfonate, trifluoromethanesulfonate, mesylate, cyanide, isocyanate, thiocyanate, tetrachloroaluminate, tetrabromoaluminate, tetrafluoroborate, hexafluorophosphate, hexafluoroantimonate, sulfate, hydroxide bis(trifluoromethanesulfonyl)imide or methyl sulfate, with the proviso that X$^-$ is absent if A is COO$^-$.

In particularly preferred imidazolium salts of the formula (II), the variables X$^-$, A, $R^1$, $R^2$, $R^3$ and $R^4$, independently of one another and in particular in combination, have the following meanings:

X$^-$ is preferably chloride, tosylate, methanesulfonate, trifluoromethanesulfonate, mesylate, tetrafluoroborate, hexafluorophosphate, hexafluoroantimonate, $C_1$-$C_{10}$-carboxylate, sulfate or methyl sulfate, in particular chloride, methanesulfonate or $C_1$-$C_{10}$-carboxylate.

A is preferably hydrogen;

$R^1$ and $R^4$, independently of one another, are preferably a radical selected from $C_1$-$C_{10}$-alkyl, $C_3$-$C_{10}$-cycloalkyl, benzyl and phenyl, where the phenyl ring in the two last-mentioned radicals is unsubstituted or is mono- or polysubstituted, e.g. mono-, di- or trisubstituted, with $C_1$-$C_3$-alkyl. In particular, $R^1$ and $R^4$ are $C_1$-$C_{10}$-alkyl, specifically $C_1$-$C_6$-alkyl;

$R^2$ and $R^3$, independently of one another, are preferably a radical selected from hydrogen, $C_1$-$C_{10}$-alkyl, $C_3$-$C_{10}$-cycloalkyl, benzyl and phenyl, where the phenyl ring in the two last-mentioned radicals is unsubstituted or is mono- or polysubstituted, e.g. mono-, di- or trisubstituted, with $C_1$-$C_3$-alkyl. In particular, $R^2$ and $R^3$ are hydrogen or $C_1$-$C_{10}$-alkyl, specifically hydrogen or $C_1$-$C_6$-alkyl and very specifically hydrogen.

Examples of suitable imidazolium salts of the formula (II) are 1,3-dimethylimidazolium salts, 1-methyl-3-isopropylimidazolium salts, 1,3-diethylimidazolium salts, 1-methyl-3-n-propylimidazolium salts, 1-methyl-4-n-butylimidazolium salts, 1,3,4,5-tetramethylimidazolium salts, 1,3-di-n-propylimidazolium salts, 1,3-diisopropylimidazolium salts, 1,3-di-n-butylimidazolium salts, 1,3-di-sec-butylimidazolium salts, 1,3-di-tert-butylimidazolium salts, 1,3-dicyclohexylimidazolium salts, 1,3-diadamantylimidazolium salts, 1,3-diphenylimidazolium salts, 1,3-ditolylimidazolium salts, 1,3-dixylylimidazolium salts, 1,3-dimesitylimidazolium salts, 1,3-bis[2,6-di(isopropyl)phenyl]imidazolium salts, in particular their chlorides, tosylates, methanesulfonates, trifluoromethanesulfonates, mesylates, tetrafluoroborates, hexafluorophosphates, hexafluoroantimonates, sulfates, $C_1$-$C_{10}$-carboxylates and methyl sulfates, specifically the chlorides, methanesulfonates and $C_1$-$C_{10}$-carboxylates.

N-Heterocyclic carbenes have similar ligand properties to trialkyl- or triarylphosphanes, but compared with phosphanes, N-heterocyclic carbenes have the advantage that they are not oxidation-sensitive. N-heterocyclic carbenes based on 1,3-substituted imidazoles are synthetically very easily accessible, see for example W. A. Herrmann, Angew. Chem. 2002, 41, 1290-1309; E. Perls, Top. Organomet. Chem. 2007, 21, 83-116; T. N. Tekavec et al., Top. Organomet. Chem. 2007, 21, 159-192; F. Glorius, Top. Organomet. Chem. 2007, 21, 1-20, to which reference is made here in their entirety.

The imidazolium salts on which the N-heterocyclic carbenes are based are commercially available and are known for example as ionic liquids and also as solvents.

The preparation of the monodentate N-heterocyclic carbene ligand from the imidazolium salt takes place in the presence of at least one base.

Suitable bases are selected, for example, from hydrides, hydroxides, carbonates, alcoholates and amides of the alkali metals, the hydrides, hydroxides, carbonates, alcoholates and amides of the alkaline earth metals, organic amines, aryllithium compounds and alkyllithium compounds.

Preferably, the bases are selected from

B1 alkali metal hydroxides, in particular LiOH, NaOH or KOH

B2 alkaline earth metal hydroxides, in particular Ca(OH)$_2$

B3 alkali metal hydrides, in particular LiH, NaH, KH

B4 alkaline earth metal hydrides, in particular CaH$_2$

B5 alkali metal aluminum hydrides, in particular LiAlH$_4$

B6 alkali metal borohydrides, in particular NaBH$_4$, LiBH$_a$

B7 alkali metal carbonates, in particular Na$_2$CO$_3$, Li$_2$CO$_3$, K$_2$CO$_3$ B8 alkali metal phosphates, in particular K$_3$PO$_4$, Na$_3$PO$_4$ B9 alkyllithium compounds, in particular n-butyllithium, methyllithium, tert-butyllithium B10 aryllithium compounds, in particular phenyllithium B11 Alkali metal alcoholates, in particular lithium methanolate, lithium ethanolate, lithium n-propylate, lithium isopropylate, lithium n-butylate, lithium isobutylate, lithium n-pentylate, lithium n-hexylate, lithium n-heptylate, lithium n-octylate, lithium benzylate, lithium phenolate, potassium methanolate, potassium ethanolate, potassium n-propylate, potassium isopropylate, potassium n-butylate, potassium isobutylate, potassium n-pentylate, potassium n-hexylate, potassium n-heptylate, potassium n-octylate, potassium benzylate, potassium phenolate, sodium methanolate, sodium ethanolate, sodium n-propylate, sodium isopropylate, sodium n-butylate, sodium isobutylate, sodium n-pentylate, sodium n-hexylate, sodium n-heptylate, sodium n-octylate, sodium benzylate, sodium phenolate, and also the constitutional isomers of the specified alkali metal alcoholates B12 alkali metal bis(trimethylsilyl)amides, in particular potassium bis(trimethylsilyl)amide, lithium bis(trimethylsilyl)amide, sodium bis(trimethylsilyl)amide B13 amines of the formula $R^5NH_2$, where $R^5$ is substituted or unsubstituted $C_1$-$C_{10}$-alkyl, $C_1$-$C_4$-alkyl-P(phenyl)$_2$, $C_3$-$C_{10}$-cycloalkyl, $C_3$-$C_{10}$-heterocyclyl, where $C_3$-$C_{10}$-heterocyclyl comprises at least one heteroatom selected from N, O and S, $C_5$-$C_{14}$-aryl or $C_5$-$C_{10}$-heteroaryl, where $C_5$-$C_{10}$-heteroaryl comprises at least one heteroatom selected from N, O and S, B14 amines of the formula $R^6R^7NH$, where $R^6$ and $R^7$, independently of one another, are substituted or unsubstituted $C_1$-$C_{10}$-alkyl, $C_1$-$C_4$-alkyl-P(phenyl)$_2$, $C_3$-$C_{10}$-cycloalkyl, $C_3$-$C_{10}$-heterocyclyl, where $C_3$-$C_{10}$-heterocyclyl comprises at least one heteroatom selected from N, O and S, $C_5$-$C_{14}$-aryl or $C_5$-$C_{10}$-heteroaryl, where $C_5$-$C_{10}$-heteroaryl comprises at least one heteroatom selected from N, O and S, B15 amines of the formula $R^8R^9R^{10}N$, where $R^8$, $R^9$ and $R^{10}$, independently of one another, are substituted or unsubstituted $C_1$-$C_{10}$-alkyl, $C_1$-$C_4$-alkyl-P(phenyl)$_2$, $C_3$-$C_{10}$-cycloalkyl, $C_3$-$C_{10}$-heterocyclyl, where $C_3$-$C_{10}$-heterocyclyl comprises at least one heteroatom selected from N, O and S, $C_5$-$C_{14}$-aryl or $C_5$-$C_{10}$-heteroaryl, where $C_5$-$C_{10}$-heteroaryl comprises at least one heteroatom selected from N, O and S.

Particular preference is given to alkali metal hydroxides, specifically potassium hydroxide, and alkaline earth metal hydroxides, and also the alkali metal alcoholates of the alcohols used in the process according to the invention, specifically potassium 3-methyl-n-butanolate and potassium 2-methyl-n-butanolate.

Specifically, potassium hydroxide is used as base.

Suitable transition metal compounds V are complex compounds and salts of the transition metals of groups 8, 9 and 10 of the Periodic Table of the Elements (IUPAC), preferably complex compounds and salts of ruthenium and of iridium, particularly preferably complex compounds and salts of ruthenium.

Particularly preferably suitable transition metal compounds V are compounds which have a transition metal atom selected from ruthenium and iridium and at least 2 ligands which are selected from p-cymene, chloride, benzene, CO, 1,5-cyclooctadiene, allyl, acetylacetonate, dimethylsulfoxide, cyclopentadienyl, pentamethylcyclopentadienyl, indenyl, cyclooctene, hydride, ethene and $H_2O$.

Suitable transition metal compounds V are, for example, [Ru(p-cymene)Cl$_2$]$_2$, [Ru(benzene)Cl$_2$]$_n$, [Ru(CO)$_2$Cl$_2$]$_n$, where n in each case is in the range from 1 to 100, [Ru(CO)$_3$Cl$_2$]$_2$ [Ru(1,5-cyclooctadiene)(allyl)], RuCl$_3$.H$_2$O, [Ru(acetylacetonate)$_3$], [Ru(dimethylsulfoxide)$_4$Cl$_2$], [Ru(cyclopentadienyl)(CO)$_2$Cl], [Ru(cyclopentadienyl)(CO)$_2$H], [Ru(cyclopentadienyl)(CO)$_2$]$_2$, [Ru(pentamethylcyclopentadienyl)(CO)$_2$Cl], [Ru(pentamethylcyclopentadienyl)(CO)$_2$H], [Ru(pentamethylcyclopentadienyl)(CO)$_2$]$_2$, [Ru(indenyl)(CO)$_2$Cl], [Ru(indenyl)(CO)$_2$H], [Ru(indenyl)(CO)$_2$]$_2$, ruthenocene, [Ru(1,5-cyclooctadien)Cl$_2$]$_2$, [Ru(pentamethylcyclopentadienyl)(1,5-cyclooctadiene)Cl], [Ru$_3$(CO)$_{12}$], IrCl$_3$.H$_2$O, KIrCl$_4$, K$_3$IrCl$_6$, [Ir(1,5-cyclooctadiene)Cl]$_2$, [Ir(cyclooctene)$_2$Cl]$_2$, [Ir(ethene)$_2$Cl]$_2$, [Ir(cyclopentadienyl)Cl$_2$]$_2$, [Ir(pentamethylcyclopentadienyl)Cl$_2$]$_2$ and [Ir(cyclopentadienyl)(CO)$_2$] and [Ir(pentamethylcyclopentadienyl)(CO)$_2$].

In the process according to the invention, a primary monoalcohol or a mixture of a primary monoalcohol and at least one alcohol different therefrom is reacted to give the carboxylic acid ester. The use of alcohol mixtures can lead to the formation of the mixed carboxylic acid esters. The reaction can be illustrated by the two following reaction equations:

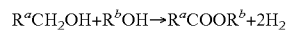

If a mixture of a primary monoalcohol and at least one alcohol different therefrom is reacted, the primary monoalcohol is preferably used in an amount of at least 50 mol %, based on the total molar amount of alcohol.

Suitable primary monoalcohols in the process according to the invention are practically all primary monoalcohols. The primary monoalcohols can be linear, branched or cyclic. The primary monoalcohols generally have 3 to 10 carbon atoms. Besides the one hydroxyl group, the primary monoalcohols generally have no further functional groups. In particular, the primary monoalcohols are primary alkanols having preferably 3 to 10 carbon atoms, primary hydroxy-$C_1$-$C_4$-alkylbenzenes, and primary hydroxy-$C_1$-$C_4$-alkyl-$C_3$-$C_8$-cycloalkanes. Specifically, the primary monoalcohols are primary alkanols having preferably 3 to 10 carbon atoms and in particular 3 to 6 carbon atoms. Suitable primary monoalcohols are, for example, 1-propanol, 1-butanol, 2-methyl-n-propanol, 1-pentanol, 3-methyl-n-butanol, 2-methyl-n-butanol, 1-hexanol, 1-heptanol, 1-octanol, 2-ethyl-n-hexanol, 2-propyl-n-heptanol, 1-hydroxymethylcyclohexane, benzyl alcohol and 2-phenylethanol. The primary monoalcohols can also be used as mixtures.

Suitable alcohols which are optionally used in mixture with the primary monoalcohol can be aliphatic, cycloaliphatic or aromatic, linear or branched. They may be secondary or tertiary alcohols. The alcohols different from the primary monoalcohols generally have 3 to 10 carbon atoms. The alcohols different from the primary monoalcohols are preferably monoalcohols and generally have no further functional groups besides the one hydroxyl group. In particular, the alcohols different from the primary monoalcohols are secondary or tertiary alkanols having preferably 3 to 10 carbon atoms, cycloalkanols having preferably 5 to 10 carbon atoms, secondary or tertiary hydroxy-$C_1$-$C_4$-alkylbenzenes and secondary or tertiary hydroxy-$C_1$-$C_4$-alkyl-$C_3$-$C_8$-cycloalkanes. Examples of such alcohols are isopropanol, 2-butanol, tert-butanol, cyclopentanol, cyclohexanol, 1-phenylethanol, phenol or 1-methyl-n-butanol.

It is also possible to use mixtures of different alcohols which are obtained from fermentative sources, for example mixtures of 3-methyl-n-butanol and 2-methyl-n-butanol which are produced as by-product in the industrial production of bioethanol (so-called "fusel oils").

The primary monoalcohols and also the optionally used further alcohols can, moreover, carry substituents which behave in an inert manner under the reaction conditions of the process according to the invention, for example alkoxy, alkenoxy, dialkylamino and halogen (F, Cl, Br, I).

In a specific embodiment of the invention, a primary aliphatic $C_3$-$C_{10}$-alcohol or a mixture of primary aliphatic $C_3$-$C_{10}$-alcohols, in particular a primary aliphatic $C_4$-$C_6$-alcohol or a mixture of primary aliphatic $C_4$-$C_6$-alcohols is reacted.

In a very specific embodiment of the invention, the primary monoalcohol reacted is isoamyl alcohol or a mixture of isoamyl alcohol with 2-methyl-n-butanol.

The process according to the invention takes place in the presence of a transition metal carbene complex catalyst K, as defined above. It has proven to be advantageous if the catalytically active part of the catalyst K is present at least partially in dissolved form in the liquid reaction medium. In a preferred embodiment, at least 90% of the catalyst K used in the process is present in the liquid reaction medium in dissolved form, particularly preferably at least 95% and very particularly preferably more than 99%, in each case based on the total amount in the liquid reaction medium.

According to the invention, the transition metal carbene complex catalyst K defined above is prepared by reacting a transition metal compound V with an imidazolium salt in the presence of the primary monoalcohol and the base.

The amount of metal component in the catalyst, preferably ruthenium or iridium, is generally 0.1 to 5000 ppm (parts by weight), in particular in the range from 1 to 2000 ppm, specifically 50 to 1000 ppm, in each case based on the total weight of the liquid reaction mixture.

The base is preferably used in an amount of from 1 to 20 equivalents of base, in particular in an amount of from 1 to 5 equivalents of base, based on 1 equivalent of the imidazolium salt.

The imidazolium salt is preferably used in an amount of from 1 to 20 mol, in particular in an amount of from 1 to 6 mol, based on 1 mol of the transition metal in the transition metal compound V.

According to the invention, the transition metal carbene complex catalyst K is prepared in the presence of the primary monoalcohol and the base. For this, the procedure generally involves introducing the primary monoalcohol or the mixture of a primary monoalcohol and at least one alcohol different therefrom, the imidazolium salt, the transition metal compound V and the base together into the reaction space, or initially introducing the primary monoalcohol or the mixture of a primary monoalcohol and at least one alcohol different therefrom and optionally the base into the reaction space and adding to this the constituents forming the catalyst and optionally base.

The reaction of the primary monoalcohol or of the mixture of a primary monoalcohol and at least one alcohol different therefrom generally takes place at a temperature in the range from 20 to 250° C. Preferably, the process according to the invention is carried out at temperatures in the range from 100° C. to 200° C., particularly preferably in the range from 110 to 200° C.

The reaction of the primary monoalcohol or the mixture of a primary monoalcohol and at least one alcohol different therefrom is generally carried out at an overall pressure of from 0.1 to 20 MPa absolute, which can be either the intrinsic pressure of the alcohols or of the alcohol at the reaction temperature or the pressure of a gas such as nitrogen, argon or hydrogen. Preferably, the process according to the invention is carried out at an overall pressure up to 10 MPa absolute, in particular at an overall pressure up to 1 MPa absolute.

According to the invention, the reaction of the primary monoalcohol or of the mixture of a primary monoalcohol and at least one alcohol different therefrom takes place without dilution, i.e. no additional solvent is added to the reaction mixture. Accordingly, the content of solvent in the reaction mixture is less than 10% by weight, preferably less than 5% by weight, particularly preferably less than 2% by weight and especially less than 1% by weight.

The reaction time is generally determined by the reaction temperature, the reactivity of the alcohols used and the desired conversion. As a rule, the reaction of the primary monoalcohol or the reaction of the mixture of a primary monoalcohol and at least one alcohol different therefrom will be conducted until the conversion, based on the primary monoalcohol, is at least 10%, in particular at least 20% and specifically at least 25%. It has proven to be advantageous to conduct the reaction not to complete conversion (100%, based on the primary monoalcohol), but only to a conversion of at most 80%, in particular at most 70%. The reaction time required for this can be ascertained by the person skilled in the art by means of routine experiments. It is generally in the range from 15 minutes to 100 h, in particular in the range from 1 h to 50 h.

The esterification of the primary alcohol or of the mixture of a primary monoalcohol and at least one alcohol different therefrom naturally takes place with the elimination of hydrogen (see reaction equations above). It has proven to be advantageous to remove the hydrogen from the reaction system. The conversions can be increased in this way. This is performed either by stripping out with the boiling unreacted alcohol or by introducing a stripping gas such as nitrogen, carbon dioxide or argon.

The reaction can be carried out in the customary devices and/or reactors known to the person skilled in the art for liquid-gas reactions in which the catalyst is present in homogeneously dissolved form in the liquid phase. For the process according to the invention it is in principle possible to use all reactors which are fundamentally suitable for gas-liquid reactions under the stated temperature and the stated pressure. Suitable standard reactors for gas-liquid and for liquid-liquid reaction systems are discussed for example in K. D. Henkel, "Reactor Types and Their Industrial Applications", Ullmann's Encyclopedia of Industrial Chemistry, 2005, Wiley-VCH Verlag GmbH & Co. KGaA, chapter 3.3: "Reactors for gas-liquid reactions", to which reference is hereby made. Examples which may be mentioned are stirred tank reactors, tubular reactors or bubble column reactors. The supply of alcohol, transition metal compound V, imidazolium salt and of base can take place here simultaneously or separately from one another. The reaction here can be carried out discontinuously in batch mode or continuously, semicontinuously with recycle or without recycle. The average residence time in the reaction space is generally 15 minutes to 100 h, in particular 1 h to 50 h.

After the reaction, the carboxylic acid ester is generally separated off from unreacted alcohol preferably by distillation. The catalyst K is retained with the high boilers in the bottom of the distillation and can be reused. Unreacted alcohol can be returned to the reaction. The thermal separation off of the alcohol or of the alcohols and also of the carboxylic acid ester takes place by the processes known to the person skilled in the art, preferably in an evaporator or in a distillation unit, comprising evaporator and column(s), which usually has a plurality of trays, packing or packing bodies.

The invention is illustrated in more detail by the examples below:

EXAMPLE 1

A 250 ml three-neck flask equipped with a water separator and a thermometer was charged with 0.21 g of [Ru(1,5-cyclooctadiene)$Cl_2]_2$, 0.7 g of 1-methyl-3-n-butylimidazolium chloride, 5 g of potassium hydroxide and 100 g of isomer mixture of 3-methyl-n-butanol and 2-methyl-n-butanol (distilled product which has been obtained from fusel oil; 80% by weight of 3-methyl-n-butanol, 20% by weight of 2-methyl-n-butanol). The mixture was heated under reflux for 20 h with stirring (magnetic stirrer) at atmospheric pressure and an oil bath temperature of 170° C. After the end of the reaction, 72.6% of unreacted starting material mixture and 27.1% of the carboxylic acid ester (isomer mixture formed from 3-methyl-n-butanol and 2-methyl-n-butanol; conversion determined by GC area %) were present in the reaction mixture. 46.3 g (mixture of starting material mixture and carboxylic acid ester) were distilled off from the reaction discharge on a rotary evaporator (80° C. oil bath temperature, 20 mbar). The catalyst and the base remained in the liquid residue and could be reused.

From the distillate of the coarse separation, the alcohol mixture was separated off from the carboxylic acid ester by means of fine distillation, giving in the bottom of the fine distillation 6.8 g of the pure carboxylic acid ester (isomer mixture) in a purity of 99.2% (determined by GC area %).

EXAMPLE 2

A 250 ml three-neck flask equipped with a water separator and a thermometer was charged with 0.21 g of [Ru(1,5-cyclooctadiene)Cl$_2$]$_2$, 0.7 g of 1-methyl-3-n-butylimidazolium chloride, 5 g of potassium hydroxide and 100 g of 1-hexanol. The mixture was heated under reflux for 20 h with stirring (magnetic stirrer) at atmospheric pressure and an oil bath temperature of 180° C. After the end of the reaction, 44.1% of unreacted starting material and 39.5% of the carboxylic acid ester (hexyl hexanoate; conversion determined by GC area %) were present in the reaction mixture. The reaction discharge can be worked up as described in example 1.

EXAMPLE 3

A 250 ml three-neck flask equipped with a water separator and a thermometer was charged with 0.21 g of [Ru(1,5-cyclooctadiene)Cl$_2$]$_2$, 0.7 g of 1-methyl-3-n-butylimidazolium chloride, 5 g of potassium hydroxide and 100 g of benzyl alcohol. The mixture was heated under reflux for 20 h with stirring (magnetic stirrer) at atmospheric pressure and an oil bath temperature of 240° C. After the end of the reaction, 10.4% of unreacted starting material, 4.7% of benzaldehyde (intermediate of the reaction) and 67.4% of the carboxylic acid ester (benzyl benzoate; conversion determined by GC area %) were present in the reaction mixture. The reaction discharge can be worked up as described in example 1.

The invention claimed is:

1. A process for preparing carboxylic acid esters, comprising reacting at least one primary monoalcohol or of a mixture of a primary monoalcohol and at least one different alcohol in the presence of a transition metal carbene complex catalyst K, in which the catalyst K comprises an atom M of at least one transition metal atom of group 8, 9 or 10 of the Periodic Table of the Elements (IUPAC) and at least one monodentate N-heterocyclic carbene ligand, in the presence of a base, wherein the catalyst K is prepared by reacting a transition metal compound V which comprises at least one transition metal atom of group 8, 9 or 10 of the Periodic Table of the Elements (IUPAC), but no carbene ligand, with an imidazolium salt in the presence of the primary monoalcohol and the base, and the reaction is carried out without dilution.

2. The process of claim 1, wherein the catalyst K comprises ruthenium or iridium as the central atom M.

3. The process of claim 1, wherein the catalyst K comprises at least one N-heterocyclic carbene ligand of the formula (I),

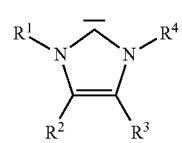

wherein
R$^1$ and R$^4$ independently of one another are C$_1$-C$_{10}$-alkyl; C$_3$-C$_{10}$-cycloalkyl; 5- to 10-membered heteroaryl with 1, 2, or 3 heteroatoms selected from O, N and S as ring members; or aryl; wherein R$^1$ and R$^4$ are unsubstituted or are optionally substituted with one or more substituents selected from halogen, C$_1$-C$_{10}$-alkoxy, CN, C$_1$-C$_{10}$-alkyl, C$_3$-C$_{10}$-cycloalkyl, phenyl, and naphthyl;
R$^2$ and R$^3$ independently of one another are hydrogen or are as defined for R$^1$ and R$^4$.

4. The process of claim 3, wherein the catalyst K comprises, in addition to at least one N-heterocyclic carbene ligand of the formula (I), at least one further ligand L selected from the group consisting of CO, hydride, aliphatic olefin, cycloolefin, carbocyclic aromatic, heteroaromatic, aldehyde, ketone, halide, C$_1$-C$_{10}$-carboxylate, methylsulfonate, methyl sulfate, trifluoromethyl sulfate, tosylate, mesylate, cyanide, isocyanate, cyanate, thiocyanate, hydroxide, C$_1$-C$_{10}$-alkoxide, cyclopentadienide, pentamethylcyclopentadienide, and pentabenzylcyclopentadienide.

5. The process of claim 1, wherein reacting the transition metal compound V with the imidazolium salt in the presence of the primary monoalcohol and the base, forms the carbine complex catalyst K, said imidazolium salt being an imidazolium salt of the general formula (II),

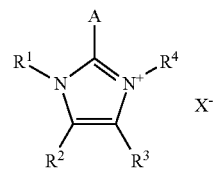

wherein
R$^1$ and R$^4$ independently of one another are C$_1$-C$_{10}$-alkyl; C$_3$-C$_{10}$-cycloalkyl; 5- to 10-membered heteroaryl with 1, 2, or 3 heteroatoms selected from O, N and S as ring members; or aryl; wherein R$^1$ and R$^4$ are unsubstituted or are optionally substituted with one or more substituents selected from halogen, C$_1$-C$_{10}$-alkoxy, CN, C$_1$-C$_{10}$-alkyl, C$_3$-C$_{10}$-cycloalkyl, phenyl, and naphthyl;
R$^2$ and R$^3$ independently of one another are hydrogen or are as defined for R$^1$ and R$^4$
A is H or COO$^-$ and
X$^-$ is the equivalent of an anion, with the proviso that X$^-$ is absent if A is COO$^-$.

6. The process of claim 5, wherein R$^1$ and R$^4$, independently of one another, are C$_1$-C$_{10}$-alkyl, R$^2$ and R$^3$ are hydrogen, and A is hydrogen.

7. The process of claim 1, wherein the base is a hydride, hydroxide, carbonate, alcoholate, or amide of an alkali metal; a hydride, hydroxide, carbonate, alcoholate, or amide of an alkaline earth metal; an organic amine; an aryllithium compound; or an alkyllithium compound.

8. The process of claim 1, wherein the base is used in an amount of from 1 to 20 equivalents of base, based on 1 equivalent of the imidazolium salt.

9. The process of claim 1, wherein the imidazolium salt is used in an amount of from 1 to 20 mol, based on 1 mol of the transition metal in the transition metal compound V.

10. The process of claim 1, wherein the transition metal compound V comprises a complex compound or a salt of ruthenium or iridium.

11. The process of claim 10, wherein the transition metal compound V comprises at least one transition metal atom selected from ruthenium and iridium and comprises at least 2 ligands selected from the group consisting of p-cymene, chloride, benzene, CO, 1,5-cyclooctadiene, allyl, acetylacetonate, dimethylsulfoxide, cyclopentadienyl, pentamethylcyclopentadienyl, indenyl, cyclooctene, hydride, ethane, and $H_2O$.

12. The process of claim 10, wherein the transition metal compound V is selected from the group consisting of [Ru(p-cymene)$Cl_2]_2$, [Ru(benzene)$Cl_2]_n$, [Ru(CO)$_2Cl_2]_n$, [Ru(CO)$_3Cl_2]_2$ [Ru(1,5-cyclooctadiene)(allyl)], $RuCl_3 \cdot H_2O$, [Ru(acetylacetonate)$_3$], [Ru(dimethylsulfoxide)$_4Cl_2$], [Ru(cyclopentadienyl)(CO)$_2$Cl], [Ru(cyclopentadienyl)(CO)$_2$H], [Ru(cyclopentadienyl)(CO)$_2]_2$, [Ru(pentamethylcyclopentadienyl)(CO)$_2$Cl], [Ru(pentamethylcyclopentadienyl)(CO)$_2$H], [Ru(pentamethylcyclopentadienyl)(CO)$_2]_2$, [Ru(indenyl)(CO)$_2$Cl], [Ru(indenyl)(CO)$_2$H], [Ru(indenyl)(CO)$_2]_2$, ruthenocene, [Ru(1,5-cyclooctadiene)$Cl_2]_2$, [Ru(pentamethylcyclopentadienyl)(1,5-cyclooctadiene)Cl], [Ru$_3$(CO)$_{12}$], $IrCl_3 \cdot H_2O$, $KIrCl_4$, $K_3IrCl_6$, [Ir(1,5-cyclooctadiene)Cl]$_2$, [Ir(cyclooctene)$_2Cl]_2$, [Ir(ethene)$_2Cl]_2$, [Ir(cyclopentadienyl)$Cl_2]_2$, [Ir(pentamethylcyclopentadienyl)$Cl_2]_2$ and [Ir(cyclopentadienyl)(CO)$_2$], and [Ir(pentamethylcyclopentadienyl)(CO)$_2$], wherein n in each case is in the range from 1 to 100.

13. The process of claim 1, wherein the transition metal compound V is used in an amount of from 0.1 to 5000 ppm parts by weight, based on 1 part by weight of the primary monoalcohols or of the mixture of a primary monoalcohol with at least one alcohol different therefrom.

14. The process of claim 1, wherein the at least one primary monoalcohol is a primary aliphatic $C_3$-$C_{10}$-alcohol and the mixture of a primary monoalcohol and at least one alcohol different therefrom is a mixture of primary aliphatic $C_3$-$C_{10}$-alcohols.

15. The process of claim 14, wherein the at least one primary monoalcohol is isoamyl alcohol and the mixture of a primary monoalcohol and at least one alcohol different therefrom is a mixture of isoamyl alcohol with 2-methylbutanol.

16. The process of claim 1, wherein the reaction of the at least one primary monoalcohol or of the mixture of a primary monoalcohol with at least one alcohol different therefrom is carried out at a temperature in the range from 20 to 250° C.

17. The process of claim 5, wherein X is halide, $C_1$-$C_{10}$-carboxylate, benzoate, $MeC_6H_4COO^-$, tosylate, methanesulfonate, trifluoromethanesulfonate, mesylate, cyanide, isocyanate, thiocyanate, tetrachloroaluminate, tetrabromoaluminate, tetrafluoroborate, hexafluorophosphate, hexafluoroantimonate, sulfate, hydroxide bis(trifluoromethanesulfonyl)imide, or methyl sulfate.

18. The process of claim 5, wherein $R^1$ and $R^4$, independently of one another, are branched $C_3$-$C_{10}$-alkyl.

19. The process of claim 5, wherein $R^1$ and $R^4$ are isopropyl.

20. The process of claim 7, wherein the base is an alkali metal hydroxide or alkali metal alcoholate.

21. The process of claim 10, wherein the transition metal compound V comprises a complex compound or a salt of ruthenium.

22. The process of claim 14, wherein the at least one primary monoalcohol is a primary aliphatic $C_4$-$C_6$-alcohol and the mixture of a primary monoalcohol and at least one alcohol different therefrom is a mixture of primary aliphatic $C_4$-$C_6$-alcohols.

* * * * *